(12) United States Patent
Koehler et al.

(10) Patent No.: US 9,192,151 B2
(45) Date of Patent: Nov. 24, 2015

(54) DUAL ACTION LETHAL CONTAINERS, SYSTEMS, METHODS AND COMPOSITIONS FOR KILLING ADULT MOSQUITOS AND LARVAE

(71) Applicant: University of Florida Research Foundation, Inc., Gainesville, FL (US)

(72) Inventors: Philip G. Koehler, Gainesville, FL (US); Ephraim V. Ragasa, Gainesville, FL (US); Roberto M. Pereira, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 190 days.

(21) Appl. No.: 13/866,656

(22) Filed: Apr. 19, 2013

(65) Prior Publication Data

US 2013/0276355 A1    Oct. 24, 2013

Related U.S. Application Data

(60) Provisional application No. 61/635,497, filed on Apr. 19, 2012, provisional application No. 61/777,766, filed on Mar. 12, 2013.

(51) Int. Cl.
*A01M 1/20* (2006.01)
*A01N 37/38* (2006.01)
(Continued)

(52) U.S. Cl.
CPC ............ *A01M 1/2005* (2013.01); *A01M 1/20* (2013.01); *A01M 1/2011* (2013.01); *A01M 1/2016* (2013.01); *A01N 37/38* (2013.01); *A01N 43/40* (2013.01); *A01N 47/22* (2013.01);
(Continued)

(58) Field of Classification Search
CPC .......... A01M 1/00; A01M 1/02; A01M 1/20; A01M 1/2016

USPC .................. 43/107, 122, 124, 131, 132.1
See application file for complete search history.

(56) References Cited

U.S. PATENT DOCUMENTS 4,103,450 A *  8/1978  Whitcomb ............... 43/131
5,401,310 A     3/1995  Ture
(Continued)

FOREIGN PATENT DOCUMENTS

| WO | 03081119 | 10/2003 |
|---|---|---|
| WO | 2011094581 | 8/2011 |
| WO | 2011145667 | 11/2011 |

OTHER PUBLICATIONS

Tikasingh, et al., A Multi-Paddle Ovitrap for Collecting *Haemagogus* and *Aedes aegypti* Eggs, Mosquito News, 1983, pp. 358-360, vol. 43, No. 3.
Kloter, et al., Evaluation of Some Ovitrap Materials Used for *Aedes aegypti* Surveillance, Mosquito News, 1983, pp. 438-439, vol. 43, No. 4.

(Continued)

*Primary Examiner* — David Parsley
(74) *Attorney, Agent, or Firm* — Brian S. Steinberger; Law Offices of Brian S. Steinberger, P.A.

(57) ABSTRACT

Dual action lethal containers, systems, methods, compositions and formulas used to kill mosquitoes and their larvae. The containers can have separate interior larvicidal and adulticidal coatings separated from each other by horizontal water line holes in the container. Another container can use a novel combined coating of a larvicidal and adulticidal coating. Unique compositions of adulticidal coatings, larvicidal coatings and combined adulticidal and larvicidal coatings can be used as liners.

35 Claims, 11 Drawing Sheets

2 - Water level holes
4 - Larvicidal coating
5 - Adulticidal coating
6 - Water Line

(51) Int. Cl.
*A01N 43/40* (2006.01)
*A01N 57/16* (2006.01)
*A01N 63/00* (2006.01)
*A01N 47/22* (2006.01)
*A01N 49/00* (2006.01)
*A01N 53/00* (2006.01)

(52) U.S. Cl.
CPC ............... *A01N 49/00* (2013.01); *A01N 53/00* (2013.01); *A01N 57/16* (2013.01); *A01N 63/00* (2013.01)

(56) References Cited

U.S. PATENT DOCUMENTS

| | | | |
|---|---|---|---|
| 5,698,210 | A | 12/1997 | Levy |
| 5,775,026 | A * | 7/1998 | Pearce et al. ................. 43/132.1 |
| 5,983,557 | A | 11/1999 | Perich |
| 6,185,861 | B1 | 2/2001 | Perich |
| 6,389,740 | B2 | 5/2002 | Perich |
| 2008/0115406 | A1 * | 5/2008 | Duston et al. ................... 43/131 |
| 2010/0043276 | A1 * | 2/2010 | Eger et al. ....................... 43/131 |
| 2010/0132245 | A1 | 6/2010 | Vestergaard |
| 2010/0158965 | A1 * | 6/2010 | Beitzel et al. ................. 424/405 |
| 2011/0289824 | A1 * | 12/2011 | Wu et al. ...................... 43/132.1 |

OTHER PUBLICATIONS

Ikeshoji, et al., Surfactants for a Mosquito Ovitrap, Jap. J. Sanit. Zool., 1977, pp. 452-452, vol. 28, No. 4.

Mogi, et al., Ovitrap Surveys of Dengue Vector Mosquitoes in Chiang Mai, Northern Thailand: Seasonal Shifts in Relative Abundance of *Aedes albopictus* and Ae.aegypti, Medical and Veterinary Entomology, 1988, pp. 319-324, vol. 2.

Zeichner, The Lethal Ovitrap: A Response to the Resurgence of Dengue and Chikungunya, U.S. Army Medical Dept Journal, 2011, retrieved on Feb. 16, 2012, retrieved from http://findarticles.com/p/articles/mi_m0VVY/is_2011_July-Sept/ai_n58163605/pg_4/.

Refrasud International, s.r.I., Refractory Innovation Technology, Carbonxide 010/LP, Jun. 2012, S. S. 172 per Martina F. s.n.—74100, Taranto, Italiy, 1 page.

International Search Report for PCT/US13/37422 filed Apr. 19, 2013, 13 pages.

University of Florida Research Foundation, Inc., Dual Action Lethal Containers and Compositions for Killing Adult Mosquitos and Larvae, European patent application No. 13778229.8-1656 European Search Report mailed Jun. 2, 2015, 7 pages.

Koehler, et al., PCT Application No. PCT/US14/23478 filed Mar. 11, 2014, Notification Concerning Transmittal of International Preliminary Report on Patentability mailed Sep. 24, 2015, 12 pages.

* cited by examiner

3 – Adulticidal + Larvicidal coating

1 - Trap Body
2 - Water level holes

DUAL ACTION LETHAL CONTAINERS, SYSTEMS, METHODS AND COMPOSITIONS FOR KILLING ADULT MOSQUITOS AND LARVAE

CROSS REFERENCE TO RELATED APPLICATIONS

This invention claims the benefit of priority to U.S. Provisional Patent Application 61/635,497 filed Apr. 19, 2012 and U.S. Provisional Patent Application 61/777,766 filed Mar. 12, 2013. The entire disclosure of each of the applications listed in this paragraph are incorporated herein by specific reference thereto.

FIELD OF INVENTION

This invention relates to killing mosquitoes, and in particular to dual action lethal containers, systems and methods of use and novel, long-lasting compositions and formulas which are used to kill adult mosquitoes and their larvae.

BACKGROUND AND PRIOR ART

Over the years, Ovitrap type containers, such as Ovitraps, have been used and deployed to control mosquitoes. See for example, U.S. Pat. Nos. 5,983,557 to Perich et al.; 6,185,861 to Perich; and 6,389,740 to Perich et al.; and Zeichner, Brian C. "The lethal ovitrap: a response to the resurgence of dengue and chikungunya", U.S. Army Medical Journal, July-September 2011. These types of Ovitraps have generally used a paper strip having insecticide that hangs within a cup filled with water up to a series of drain holes. The insecticide strip will hang into the water, with the intention of killing female mosquitoes as they land on the Ovitrap to lay eggs. However, these types of Ovitraps have limitations due to the insecticide on the paper breaking down rapidly because of water contact, and also the trap is not designed to kill larvae.

For example, these traps have lacked the use of a timed release of insecticide, and the water ended up breaking down the insecticide to become ineffective or not killing fast enough to prevent egg laying because of insecticide resistance in the mosquito population. A study in Key West, Fla. that used thousands of Ovitraps ended up producing mosquitoes from these water filled containers. Additionally, the Ovitraps only used an adulticide which was not effective in killing mosquito larvae.

FIG. 1 shows an example of a prior art lethal Ovitrap that uses a strip of paper, P, having insecticide thereon, that hangs into a water, W, filled container, C.

Thus, the need exists for solutions to the above problems with the prior art.

SUMMARY OF THE INVENTION

A primary objective of the present invention is to provide dual action lethal containers, systems and methods which are used to kill adult mosquitoes and their larvae.

A secondary objective of the present invention is to provide novel, long-lasting coatings, compositions and formulas that can be used to kill both adult mosquitoes and their larvae.

A third objective of the present invention is to provide dual action Ovitrap containers, systems and methods which kills both adult females, that seek the ovitrap as a location to lay eggs, as well as larvae, from any eggs that may be laid by the mosquito females before they are killed by the adulticide treatment.

A fourth objective of the present invention is to provide long lasting insecticidal coatings as container linings that can prevent quick degradation of insecticidal activity which occurs when insecticides are applied directly to surfaces of lethal ovitraps.

A fifth objective of the present invention is to provide for the use of slow release insecticide coatings as liners in containers so that pesticide exposure by humans is minimized when treated surfaces are accidentally contacted.

A sixth objective of the present invention is to provide for the use of slow release insecticide coatings as liners in containers which use different active ingredients for elimination of adults and larvae can delay development of pesticide resistance in mosquito populations and provide more efficient control of disease vectors.

A seventh objective of the present invention is to provide for the use of slow release insecticide coatings as liners in containers which can minimize environmental contamination, non-target exposure and chances of accidental insecticide poisoning to humans and animals.

The use of long-lasting insecticidal coating provides long-lasting control, as opposed to direct application of insecticides to internal surfaces of lethal ovitraps. The invention has the addition of larvicide to lethal ovitraps.

An additive can be added to the coating to enhance stability of the insecticide active ingredients and allows slow release of insecticide for a prolonged deployment of the trap in field situations.

Types of additives can include but are not limited to CARBONXIDE™ (a mixture of saturated and unsaturated hydrocarbons, and other compounds, which is an antioxidant that affects the microporosity of materials and prevents effects of aging), the additive of which is described in U.S. Pat. No. 5,401,310 to Ture, which is incorporated by reference in its' entirety. CARBONXIDE™ has been manufactured by Refrasud International s.r.l., a refractory innovation technology company, from Taranto, Italy. Other types of additives can include synergists, such as but not limited to Piperonyl butoxide (PBO), MGK-264, Etofenprox and Pyrethrins.

A synergist can be added to the long-lasting coating to overcome insecticide resistance in mosquito populations. The coating not only can protect the insecticidal active ingredient, but also synergists from degradation over time. Additionally, a combination of both an adulticide and a larvicide with a different mode of action in a single coating could allow for easier manufacturing.

The dual action ovitrap can be sold both in the retail market, for use by homeowners who need to eliminate mosquitoes from their property, and professional market, for use by mosquito control districts, pest control operators, the armed forces, humanitarian institutions and others involved in the control of mosquitoes in different situations.

The long-lasting insecticide coatings can be marketed for other uses where insect control is desired. Such coating could be used in external building walls, internal walls, and any other surfaces where mosquitoes and other pestiferous insects may rest and congregate.

The dual action lethal Ovitrap type containers can be used to kill mosquitoes and their larvae. The inside of a cup can be covered with insecticidal coating. The inner, upper surface can be coated with insecticide that kills adult mosquitoes as they land to lay eggs, and the inner lower surface can be coated with larvicide that kills larval mosquitoes that could emerge from eggs, or the interior of the trap can be coated with a combination of adulticide and larvicide.

Adult mosquitoes are attracted to water inside the cup to lay eggs. When they land on the coated surface, they are killed. If they lay eggs before they die, the larvae that hatch from the eggs are killed with the larvicide. The insecticide and larvicide can be mixed in a special coating material which prevents the insecticides from breaking down. Also the coating is designed to provide a timed release of the insecticides.

The insecticidal coatings can have colors incorporated that are attractive to mosquitoes. This dual action lethal ovitrap would be useful for control of mosquitoes that vector dengue, west Nile virus, yellow fever, and other pathogens.

Embedding the insecticides in coatings within our dual action lethal Ovitrap can protect the active ingredient and/or synergist from degradation by the water in the Ovitrap, and results in slow release of the active ingredient over time to kill mosquitoes. If the mosquitoes lay eggs before they die, a larvicide also embedded in the coating, is protected from degradation, and slowly releases over time to kill any larvae that hatch from the mosquito eggs. The dual action of the Ovitrap assures that the device will not produce mosquitoes as a result of degradation of the adulticide active ingredients.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Figure 1:
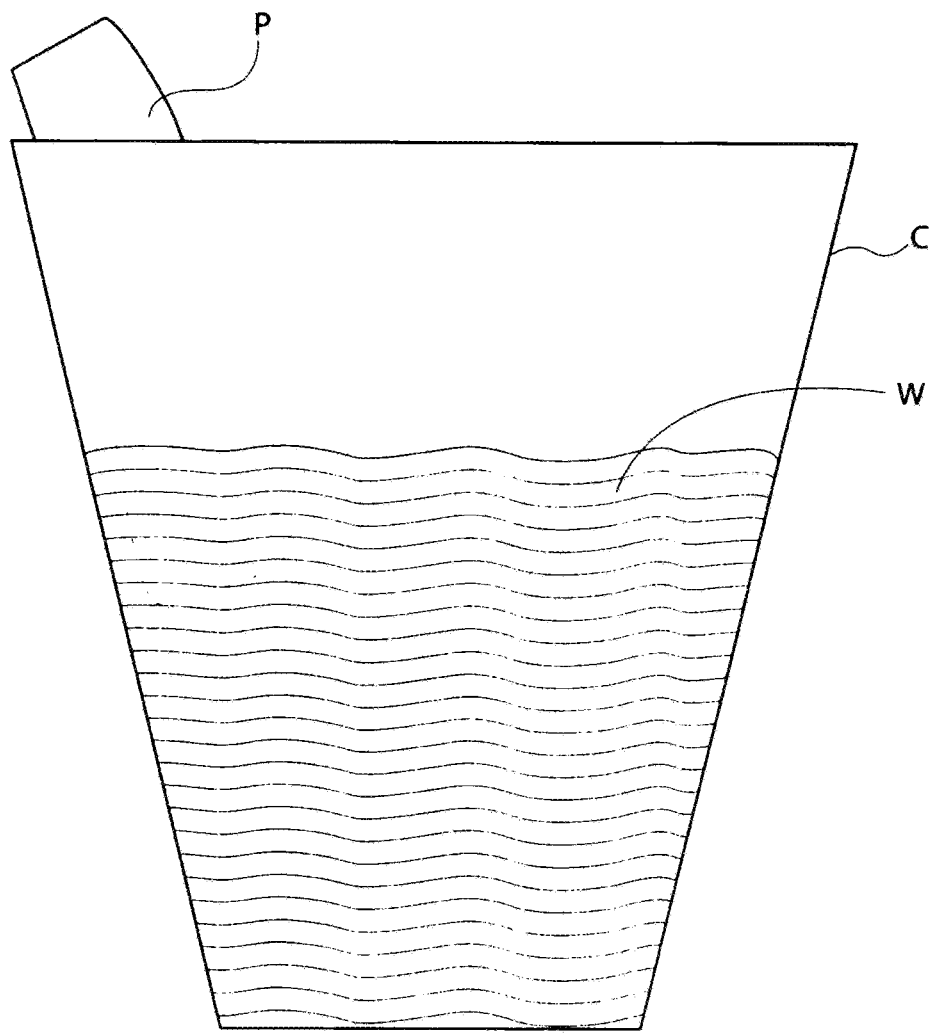
FIG. 1 shows a prior art lethal ovitrap that uses a strip of paper with insecticide hanging in a water-filled container.
Figure 2:
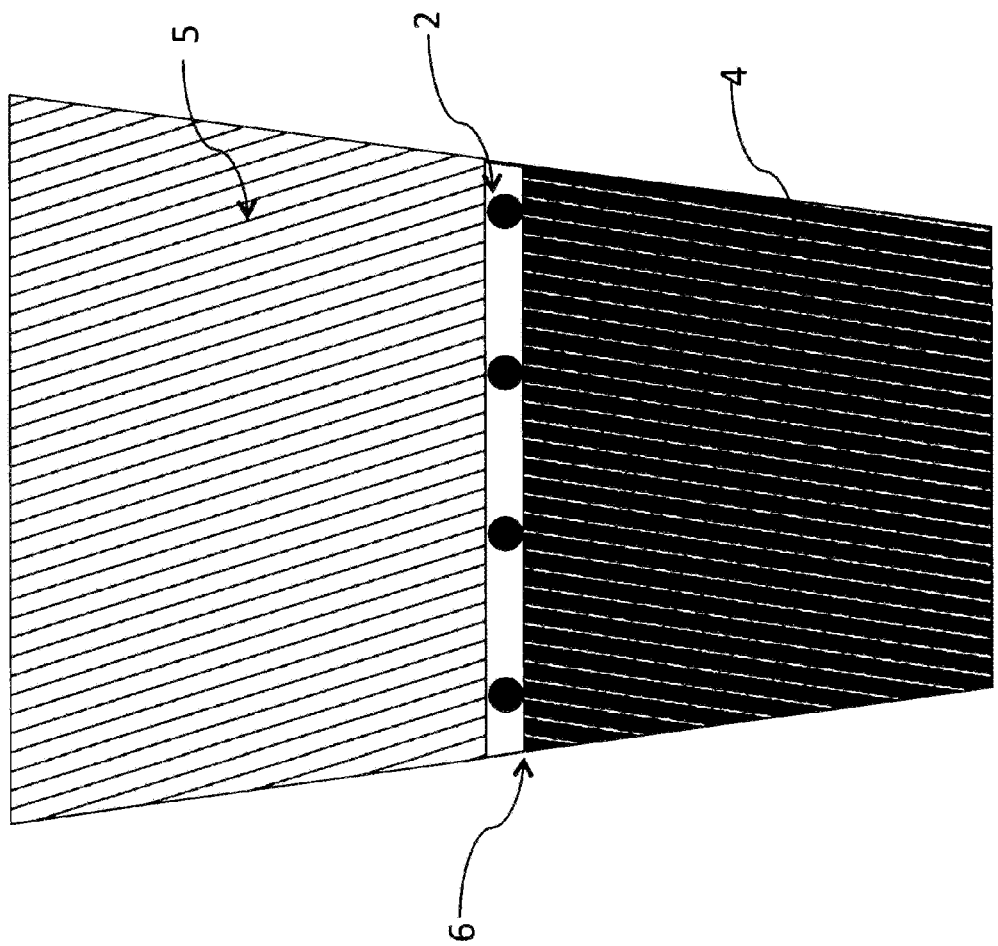
FIG. 2 is a side cross-sectional view of a novel container with two different interior layers coatings, with a novel adulticidal coating around an upper portion of the container above the holes, and a novel larvicidal coating around a lower portion of the container below the series of holes.

FIG. 2 shows a side cross-sectional view of a novel container having the two different layers 4, 5, on the interior of the container, with novel adulticidal coating 5, around an upper portion of the container above the holes 2, and a novel larvicidal coating 4, around a lower portion of the container below the series of holes 2. The container can be similar to the container C, shown in FIG. 1. Above a horizontal series of water level holes 2 can be an adulticidal coating 5, and below the water level holes 2 can be a larvicidal coating 4. The holes 2 can maintain the water line level 6 within the container.

The Steps to create an ovitrap with separate adulticide and larvicide layers can include the following:
 i. Obtain a preferred coating basis;
 ii. Prepare adulticide coating by adding adulticide active ingredient, and, if desired, the additive (CARBONXIDE™) and any synergist;
 iii. Prepare larvicidal coating by adding larvicide active ingredient, and, if desired, the additive (CARBONXIDE™) and any synergist;
 iv. Coat the bottom half of a container (8-32 oz.) internally, with the larvicidal coating;
 v. Coat the top half of a container internally with the adulticidal coating;
 vi. Drain holes can be added to the container wall at the midway line between the top adulticide coating and the bottom larvicide coating; and vii. Attachment devices such as cords, hooks, etc can be added to assist in securing the dual action ovitrap to field locations.

Figure 3:
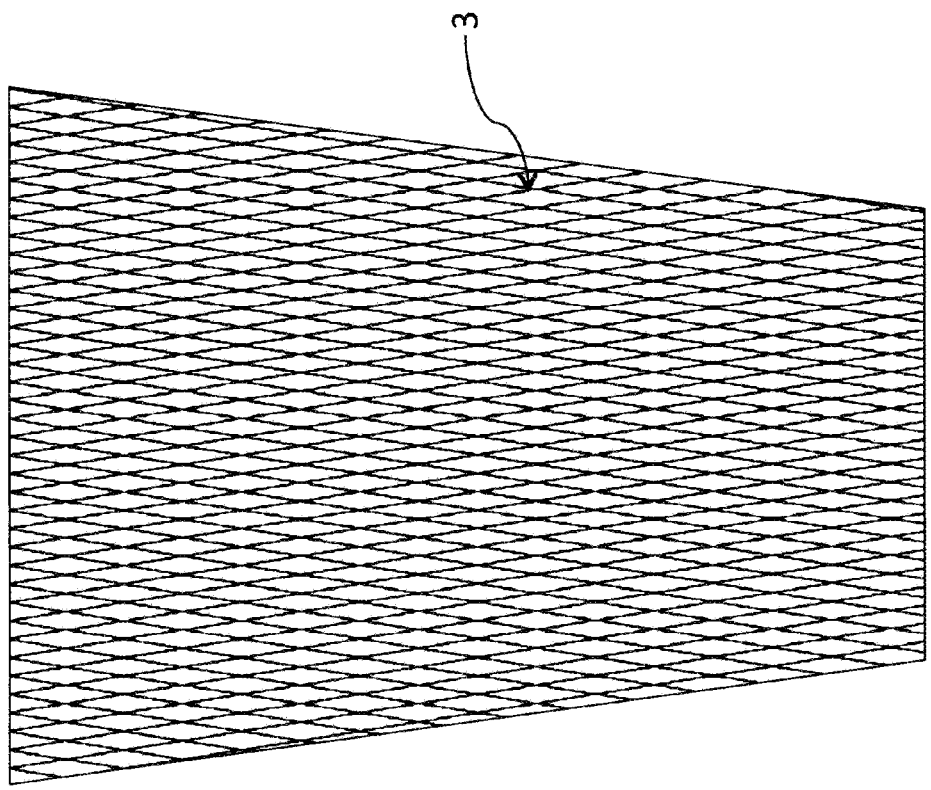
FIG. 3 is a side cross-sectional view of another novel container having a novel combined adulticidal and larvicidal coating on the interior of the container.

FIG. 3 shows a side cross-sectional view of another novel container having a combined adulticidal and larvicidal coating 3 on the interior walls of the container.

The steps to create an ovitrap with combined adulticide and larvicide layer can include:
 i. Obtain preferred coating basis;
 ii. Prepare coating by adding adulticidal and larvicidal active ingredients, and, if desired, the additive (CARBONXIDE™) and any synergist;
 iii. Coat a container (8-32 oz.) internally, with the combined adulticide/larvicide coating;
 iv. Drain holes can be added to the container wall at the midway line of the coating to prevent water from completely filling the container; and
 v. Attachment devices such as cords, hooks, etc can be added to assist in securing the dual action ovitrap to field locations.

Figure 4:
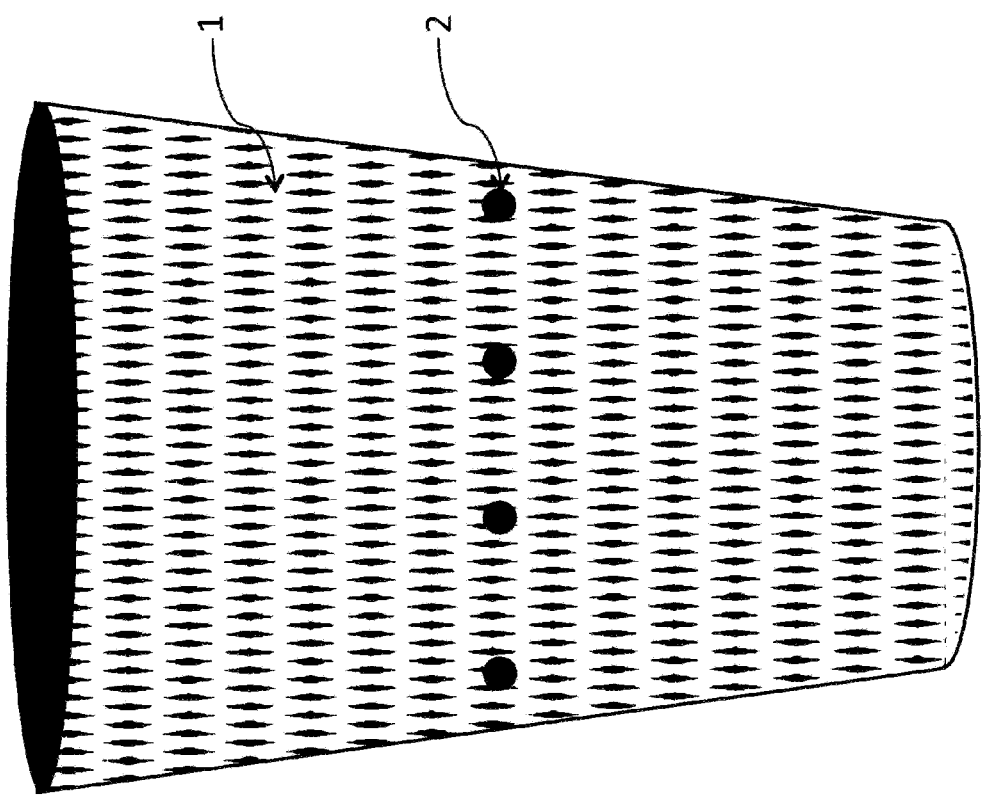
FIG. 4 is a side outside view of the FIGS. 2 and 3 containers showing the exterior walls of the container above and below the series of holes.
Figure 5:
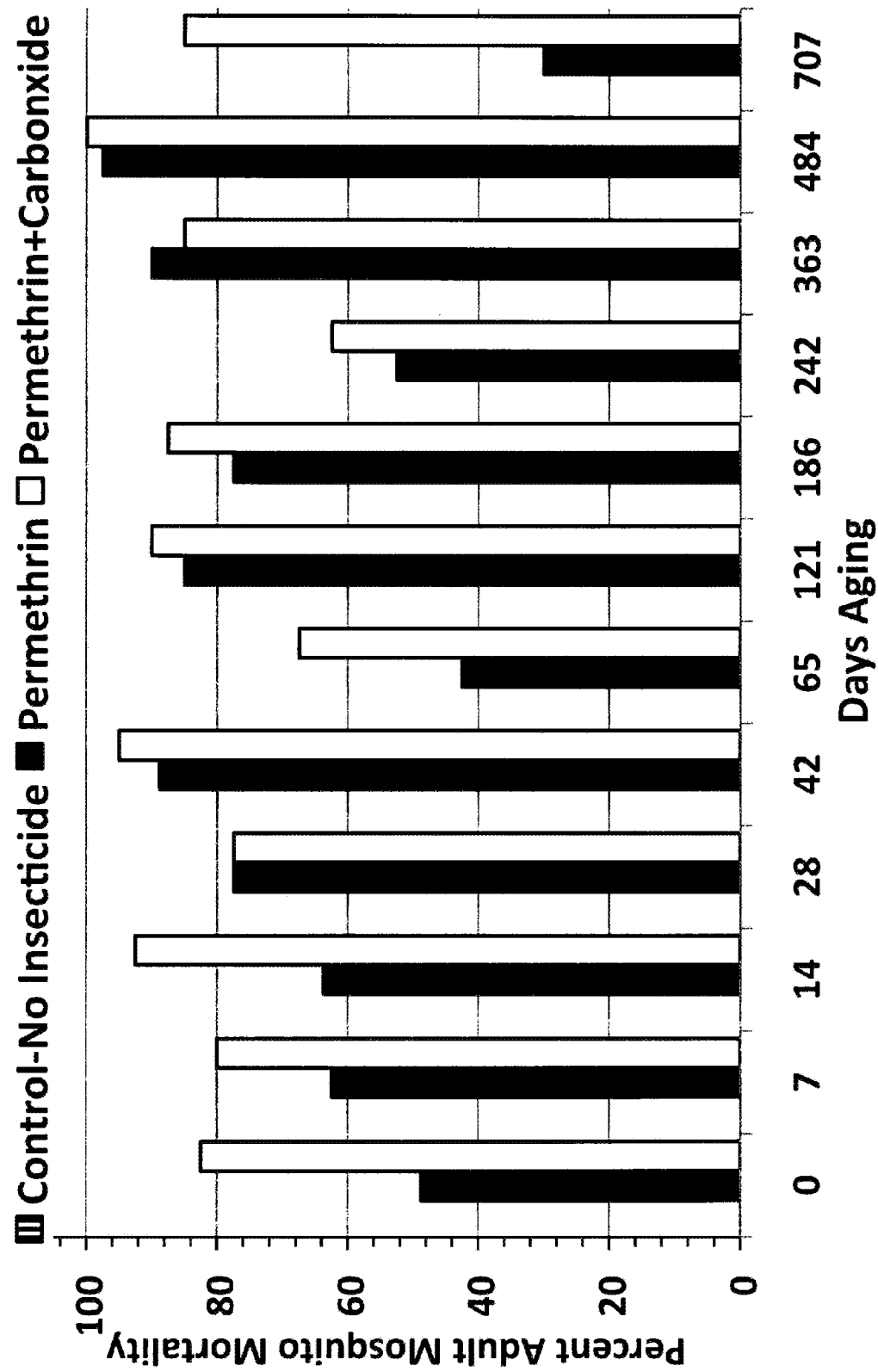
FIG. 5 shows bar graphs of Percent of Adult Mosquito Mortality versus Days Aging of the coating, for the mosquito *Aedes aegypti* after 2 hours of exposure to coatings containing either the insecticide permethrin alone or the coating combination of permethrin with a CARBONXIDE™ additive.
Figure 6:
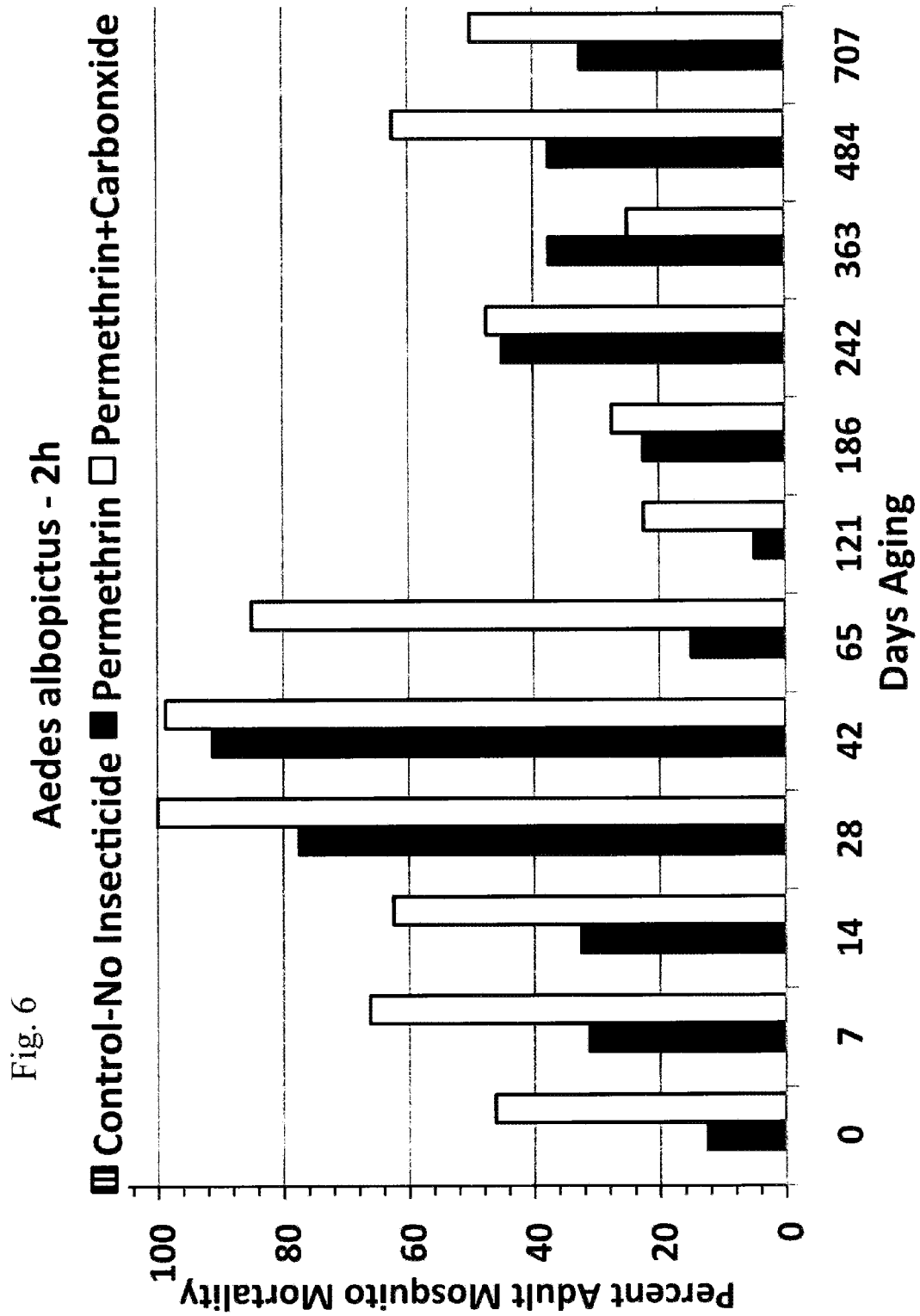
FIG. 6 shows bar graphs of Percent of Adult Mosquito Mortality versus Days Aging of the coating, for the mosquito *Aedes albopictus* after 2 hours of exposure to coatings containing either the insecticide permethrin alone or the coating combination of permethrin with a CARBONXIDE™ additive.
Figure 7:
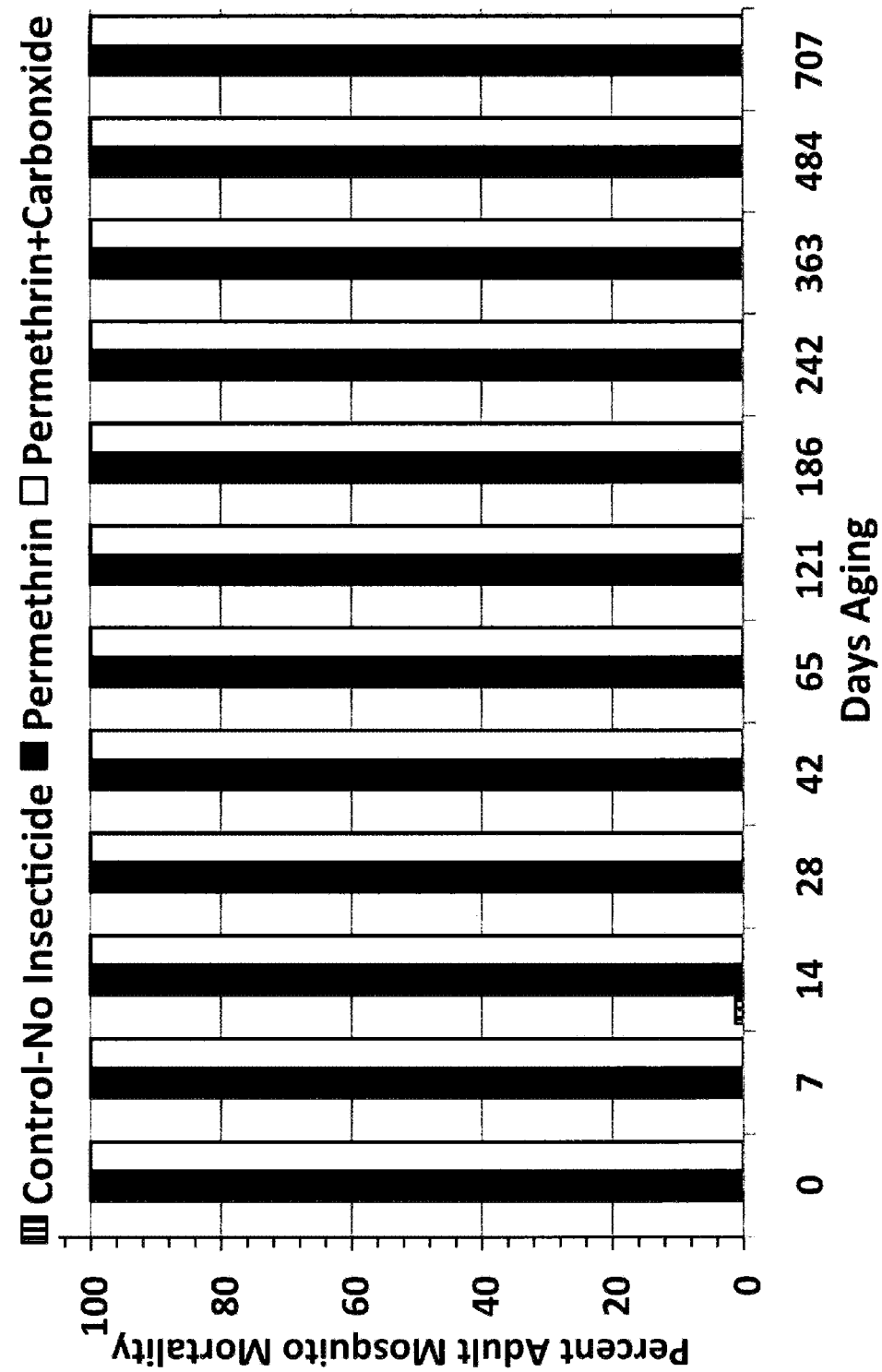
FIG. 7 shows bar graphs of Percent of Adult Mosquito Mortality versus Days Aging of the coating, for the mosquito *Aedes aegypti* after 24 hours of exposure to coatings containing either the insecticide permethrin alone or the coating combination of permethrin with a CARBONXIDE™ additive.

FIG. 4 shows a side outside view of FIGS. 2 & 3 containers side walls 1 above and below the series of drain holes 2.

The following protocols A, B, C and D list the flowchart methodologies for experiments that were conducted for evaluating the different coatings used.

A. Flowchart of Methodology in the Evaluation of Adulticide Coating Includes the Steps of:

i. Obtain preferred coating basis;
ii. Add adulticide (pyrethroids) and, if desired, an additive (CARBONXIDE™) to formulate different formulations of insecticides;
iii. Add coating on wood panels;
iv. Age wood panels in simulated environmental conditions;
v. Prepare housing for adult mosquitoes
  a Place a 4-oz plastic cup upside down on coated wood panels;
vi. Place adult mosquitoes in the housing cup to expose them to insecticidal coating;
vii. Measure mosquito mortality in 1-hour, 2-hour, and 24-hour after exposure;
viii. Collect data and perform statistical analysis to determine effectiveness of adulticide coating.

B. Flowchart of Methodology in the Evaluation of Larvicide Coating can Include:

i. Obtain preferred coating basis;
ii. Add larvicide (insect growth regulators) and, if desired, an additive (CARBONXIDE™);
iii. Coat filter paper and let air dry for 1-3 days;
iv. Prepare housing for larval mosquitoes;
  a. Place coated filter paper in 4-oz glass jars;
  b. Fill jars with unchlorinated or distilled water;
v. Place larval mosquitoes on the jars;
vi. Measure mosquito larva mortality in 12-hour intervals until all are dead or emerged as adults;
vii. Collect data and perform statistical analysis to determine effectiveness of adulticide coating.

C. Flowchart of Methodology in Evaluation of Adulticide Coating as Applied in Lethal Ovitrap can Include:

i. Obtain preferred coating basis;
ii. Add adulticide (pyrethroids) and, if desired an additive (CARBONXIDE™);
iii. Coat filter paper and let air dry for 1-3 days;
iv. Prepare oviposition cup;
  a. Place coated filter paper in a 4-oz plastic cup;
  b. Fill cup halfway with unchlorinated or distilled water;
v. Prepare housing for gravid ("pregnant") females;
  a. Cut a 1-inch hole on the side of a 3-gallon bucket;
  b. Cover hole with % in foam;
vi. Place oviposition cup in the gravid female housing bucket;
vii. Cover bucket with netting to prevent mosquito adult escape;
viii. Place gravid females in the gravid female housing bucket;
viiii. Measure mosquito mortality in 12-hour intervals until eggs were laid on the oviposition cups;
ix. Count number of eggs on filter paper;
x. Collect data and perform statistical analysis to determine effectiveness of adulticide coating.

D. Flowchart of Methodology in Evaluation of Dual-Action Ovitrap can Include:

i. Obtained preferred coating basis;
ii. Add adulticide (pyrethroids), larvicide (insect growth regulator), and, if desired, an additive (CARBONXIDE™);
  a. Also prepare coating with only adulticide or only larvicide to serve as comparison;
iii. Coat filter paper and let air dry for 1-3 days;
iv. Prepare oviposition container;
  a. Place coated filter paper in a 4-oz plastic cup;
  b. Fill cup halfway with unchlorinated or distilled water;
v. Prepare housing for gravid ("pregnant") females;
  a. Cut a 1-inch hole on the side of a 3-gallon bucket;
  b. Cover hole with % in foam;
vi. Add larval mosquitoes on the oviposition containers;
vii. Place oviposition container on the housing bucket;
viii. Cover bucket with netting to prevent mosquito adult escape;
ix. Place gravid females on the housing bucket;
x. Measure adult and larval mosquito mortality in 12-hour intervals until all larvae are dead or emerged as adults;
xi. Count number of eggs on filter paper;
xii. Collect data and perform statistical analysis to determine effectiveness of adulticide coating.

Protocols A and B referenced above were used as proof-of-concept experiments before the dual-action ovitraps were developed. Insects were exposed to aged insecticidal coatings during the tests.

Protocol C was used to test effect of the adulticide-only coating on adult mosquitoes exposed to treated ovitrap.

Protocol D was used to test adulticide-larvicidal combination in dual action ovitrap. For this experiment, coating containing just adulticide and just larvicide were also used to provide information on the effects of each product alone.

Experiment: 2h_Mort_*A*_*aegypti*_Aged_coating description

FIG. 5 shows bar graphs of Percent of Adult Mosquito Mortality versus Days Aging of the coating, for the mosquito *Aedes aegypti* after 2 hours of exposure to coatings containing either the insecticide permethrin alone or the coating combination of permethrin with the additive CARBONXIDE™. Mortality of the mosquito *Aedes aegypti*, after 2 hour of exposure to coatings containing either the insecticide permethrin alone or in combination with the additive CARBONXIDE™, was between 30 and 100% independent of the age of the coating application. Coating with additive almost always produced higher mosquito mortality than coatings without the additive. Control mortality was minimal in all experiments with aged coatings.

For all aging experiments, short-term aging was obtained by storing coated wood panels in lab at room temperature (22° C.), but long-term aging (>24 days) was obtained by placing coated wood panels in oven at 60° C. where 1 day of accelerated age corresponds approximately to 10 days at 22° C.

Experiment: 2h_Mort_*A*_*albopictus*_Aged_coating_description

FIG. 6 shows bar graphs of Percent of Adult Mosquito Mortality versus Days Aging of the coating, for the mosquito *Aedes albopictus* after 2 hours of exposure to coatings containing either the insecticide permethrin alone or the coating combination of permethrin with the additive Carbonxide. Mortality of the mosquito *Aedes albopictus*, after 2 hour of exposure to coatings containing either the insecticide permethrin alone or in combination with the additive Carbonxide, was between 10 and 100% independent of the age of the coating application. Coating with additive almost always produced higher mosquito mortality than coatings without the additive.

Experiment: 24h_Mort_*A*_*aegypti*_Aged_coating description

FIG. 7 shows bar graphs of Percent of Adult Mosquito Mortality versus Days Aging of the coating, for the mosquito *Aedes aegypti* after 24 hours of exposure to coatings containing either the insecticide permethrin alone or the coating combination of permethrin with the additive Carbonxide. 100% *A. aegypti* mosquito mortality was obtained at 24 h exposure to all the insecticidal coatings independent of aging for approximately 2 years or composition of the coating.

Experiment: 24h_Mort_A_albopictus_Aged_coating description

Figure 8:
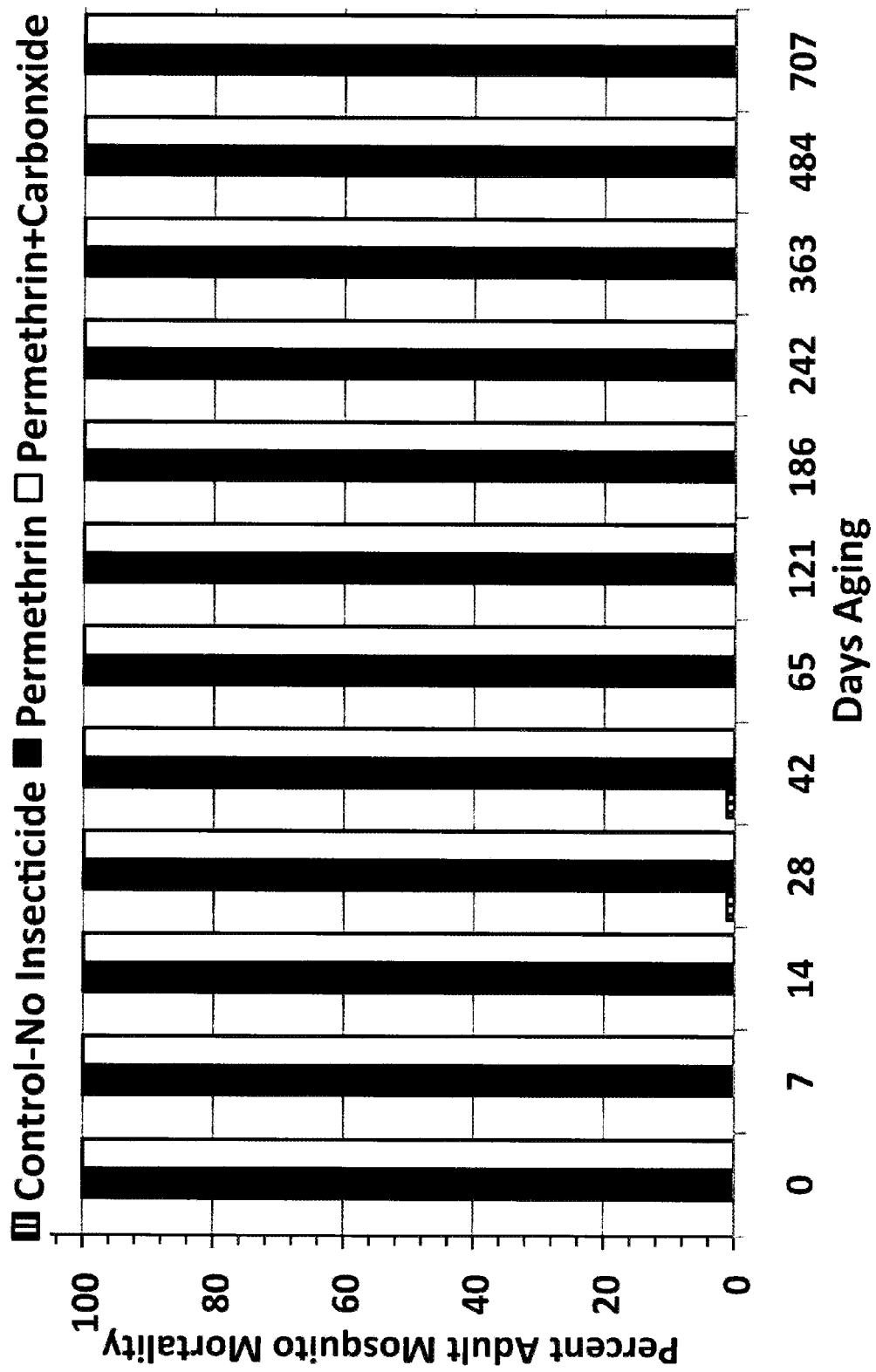
FIG. 8 shows bar graphs of Percent of Adult Mosquito Mortality versus Days Aging of the coating, for the mosquito *Aedes albotpictus* after 24 hours of exposure to coatings containing either the insecticide permethrin alone or the coating combination of permethrin with a CARBONXIDE™ additive.

FIG. 8 shows bar graphs of Percent of Adult Mosquito Mortality versus Days Aging of the coating, for the mosquito *Aedes albotpictus* after 24 hours of exposure to coatings containing either the insecticide permethrin alone or the coating combination of permethrin with the additive Carbonxide. A 100% *A. albopictus* mosquito mortality was obtained at 24 h exposure to all the insecticidal coatings independent of aging for approximately 2 years or composition of the coating.

Experiment: Per_pyri_Graph description

Figure 9:
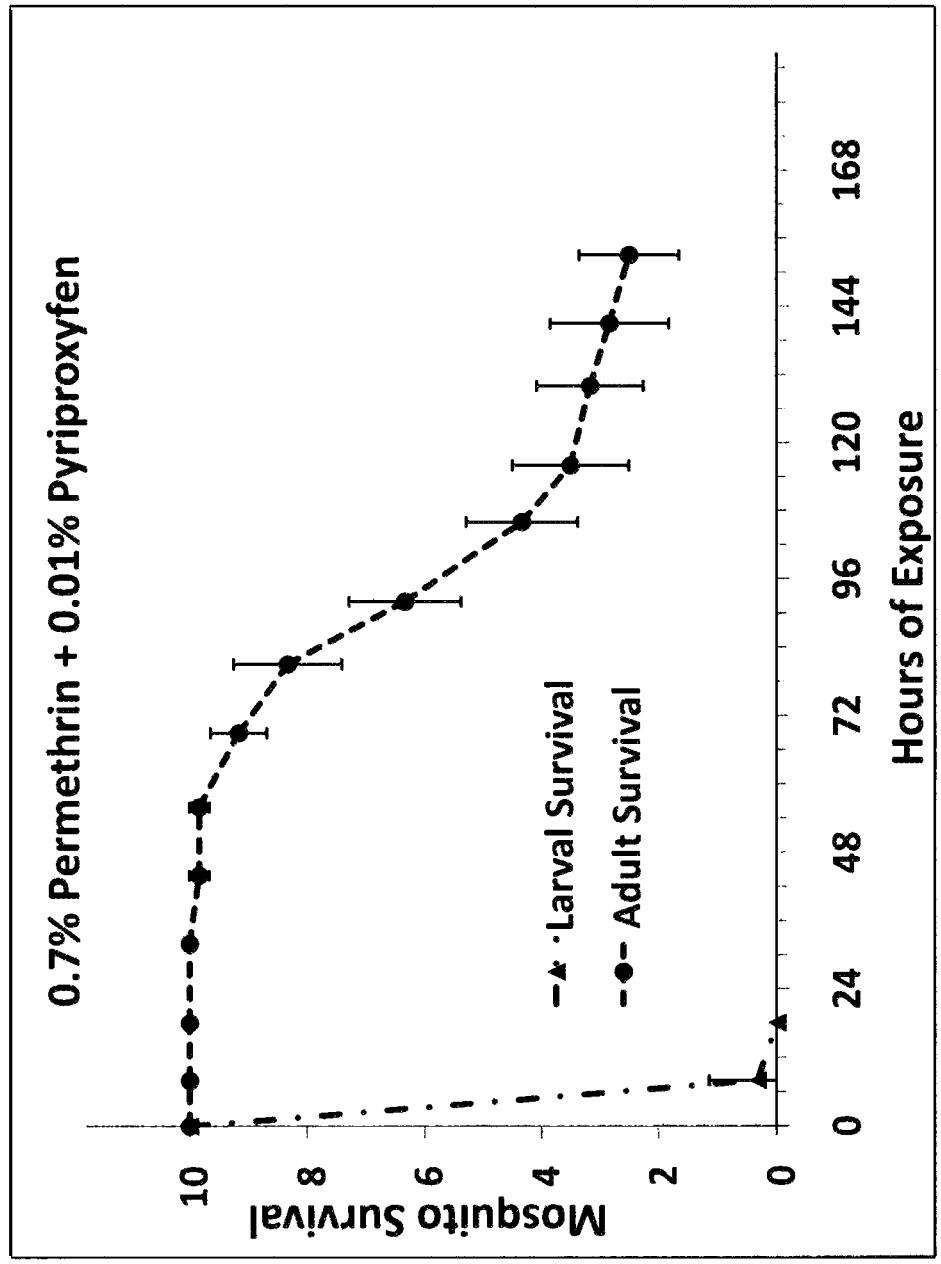
FIG. 9 is a graph of mosquito larval and adult survival versus hours of exposure to an Ovitrap treated with a coating containing both permethrin and pyriproxyfen.

FIG. 9 is a graph of mosquito larval and adult survival versus hours of exposure to an Ovitrap treated with a coating containing both permethrin and pyriproxyfen. When an ovitrap is treated with a coating containing both permethrin, which is used mainly as an adulticide but has larvicidal action, and pyriproxyfen, a larvicide with no effect as adulticide, mosquito larvae are killed rapidly, whereas adult mortality does not occur until after the females have started laying eggs, and therefore get exposed to the adulticide. Larval mortality is due to release of a combination of permethrin and pyriproxyfen into the water where larvae live. Adult mortality is only due to the pick up of permethrin when gravid females land on the side walls of the ovitrap when attempting to lay eggs.

Figure 10:
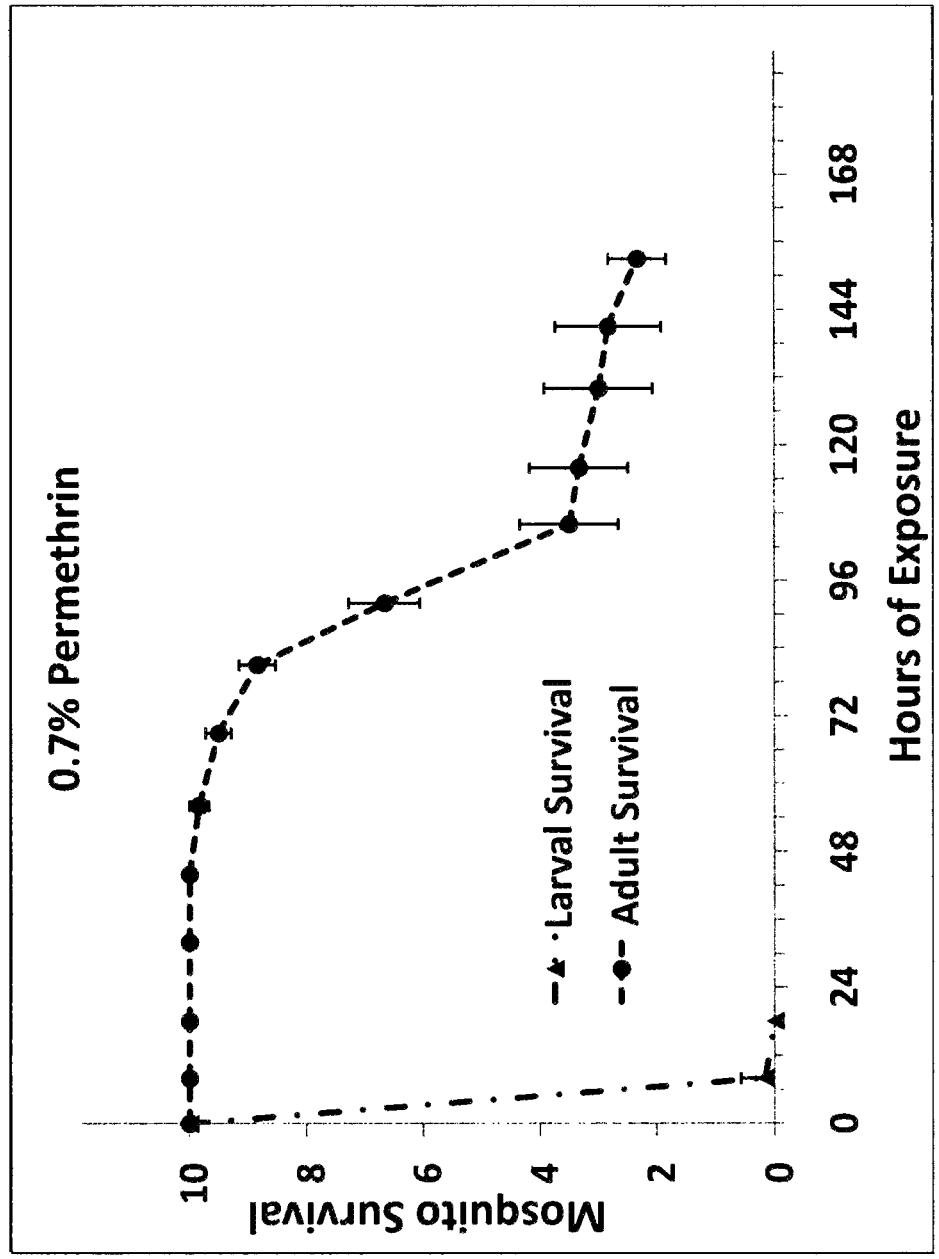
FIG. 10 is a graph of mosquito larval and adult survival versus hours of exposure to an Ovitrap treated with a coating containing only permethrin.

FIG. 10 is a graph of mosquito larval and adult survival versus hours of exposure to an Ovitrap that was treated with a coating containing only permethrin. When an ovitrap is treated with a coating containing only permethrin, which is used mainly as an adulticide but has larvicidal action, mosquito larvae are killed rapidly, due to release of permethrin into the water where larvae live. Adult mortality does not occur until after the females have started laying eggs, and therefore get exposed to the adulticide due to the pick up of permethrin by gravid females landing on the side walls of the Ovitrap.

Figure 11:
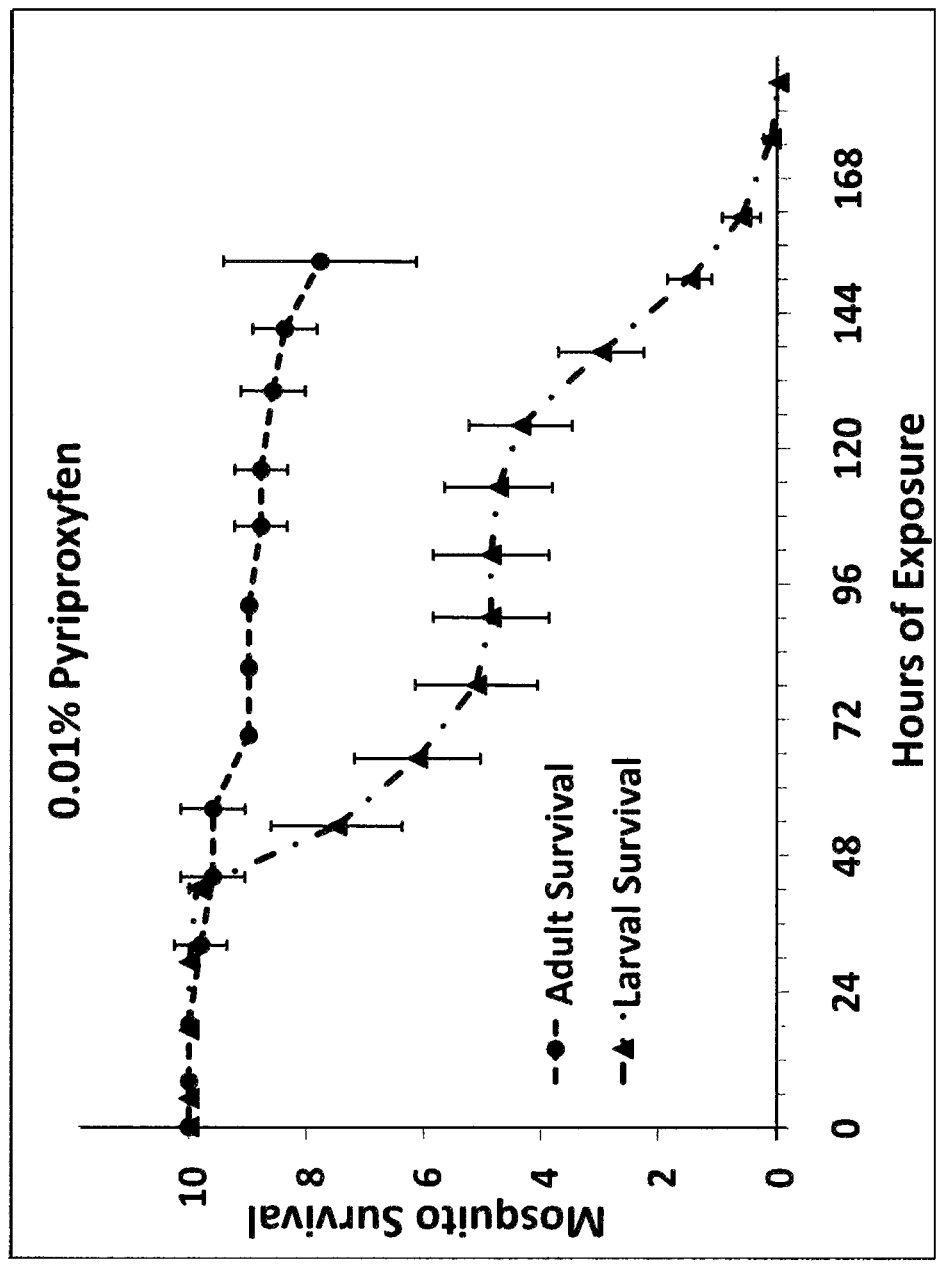
FIG. 11 is a graph of mosquito larval and adult survival versus hours of exposure to an Ovitrap treated with a coating containing only pyriproxyfen.

FIG. 11 is a graph of mosquito larval and adult survival versus hours of exposure to an Ovitrap that was treated with a coating containing only pyriproxyfen. When an ovitrap is treated with a coating containing only pyriproxyfen, a larvicide with no effect as adulticide, mosquito larvae are killed rapidly when they start molting into the pupal stage. Pyriproxyfen interferes with the development process and prevents pupal development so adults never emerge. Adults suffer only normal mortality since pyriproxyfen has no adulticide effect because adults do not go through the pupation process.

Table 1 lists the main components along with a range for each components and preferred percentage for combined adulticidal and larvicidal coating that can be used as a single lining in a container.

TABLE 1

| Main Ingredients | Choice Ingredients | Preferred Range | Preferred Exemplary Amount |
|---|---|---|---|
| Choice of Coating | | 79.0-99.9989% | 96.59% |
| | Acrylic paint | | |
| | Oil based paint | | |
| | Plastic polymer | | |
| CARBONXIDE ™ or other additive | | 0-4.0% | 2.0% |
| Choice of Adulticidal Active Ingredient: | | 0.001-5.0% | 0.7% |
| | Pyrethroid insecticide | | |
| | Organophosphate insecticide | | |
| | Carbamate insecticide | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Larvicidal Active Ingredient: | | 0.0001-2% | 0.01% |
| | *Bacillus thuringiensis israelensis* | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 2 lists the main components along with a range for each components and preferred percentage for an adulticidal coating.

TABLE 2

| Main Ingredients | Choice Ingredients | Preferred Range | Preferred Exemplary Amount |
|---|---|---|---|
| Choice of Coating | | 81.0-98.999% | 96.6% |
| | Acrylic paint | | |
| | Oil based paint | | |
| | Plastic polymer | | |
| CARBONXIDE ™ or other additive | | 0-4.0% | 2.0% |
| Choice of Adulticidal Active Ingredient: | | 0.001-5.0% | 0.7% |
| | Pyrethroid insecticide | | |
| | Organophosphate insecticide | | |
| | Carbamate insecticide | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 3 lists the main components along with a range for each components and preferred percentage for larvicidal coating.

TABLE 3

| Main Ingredients | Choice Ingredients | Preferred Range | Preferred Exemplary Amount |
|---|---|---|---|
| Coating (choice of one) | | 84.0-99.9999% | 97.82% |
| | Acrylic paint | | |

TABLE 3-continued

| Main Ingredients | Choice Ingredients | Preferred Range | Preferred Exemplary Amount |
|---|---|---|---|
| | Oil based paint | | |
| | Plastic polymer | | |
| CARBONXIDE ™ or other additive | | 0.0-4.0% | 2.0% |
| Choice of Larvicidal Active Ingredients: | | 0.0001-2% | 0.01% |
| | Bacillus thuringiensis israelensis | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of 1-3 Synergists: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 4 lists additional examples of adulticide and larvicidal coating ingredients that can be used in the interior coatings of the container along with a range for each components and preferred percentage for combined adulticidal and larvicidal coating.

TABLE 4

| Main Ingredients | Choice Ingredients | Preferred Range | Preferred Exemplary Amount |
|---|---|---|---|
| Choice of Coating | | 83.0-99.9989% | 98.59% |
| | Acrylic paint | | |
| | Oil based paint | | |
| | Plastic polymer | | |
| Choice of Adulticidal Active Ingredient: | | 0.001-5.0% | 0.7% |
| | Pyrethroid insecticide | | |
| | Organophosphate insecticide | | |
| | Carbamate insecticide | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Larvicidal Active Ingredient: | | 0.0001-2% | 0.01% |
| | Bacillus thuringiensis israelensis | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 5 lists the main components along with a range for each components and preferred percentage for an adulticidal coating.

TABLE 5

| Main Ingredients | Choice Ingredients | Preferred Range | Preferred Exemplary Amount |
|---|---|---|---|
| Choice of Coating | | 85.0-98.999% | 98.6% |
| | Acrylic paint | | |
| | Oil based paint | | |
| | Plastic polymer | | |
| Choice of Adulticidal Active Ingredient: | | 0.001-5.0% | 0.7% |
| | Pyrethroid insecticide | | |
| | Organophosphate insecticide | | |
| | Carbamate insecticide | | |
| | Permethrin (pyrethroid) | 0.2-5.0% | 0.7% |
| | Cypermethrin (pyrethroid) | 0.02-5.0% | 0.1% |
| | Deltamethrin (pyrethroid) | 0.001-5% | 0.06% |
| | Bifenthrin (pyrethroid) | 0.001-5% | 0.06% |
| | Chlorpyrifos (organophosphate) | 0.2-5.0% | 0.5% |
| | Propoxur (carbamate) | 0.2-5.0% | 0.5% |
| | Diazinon (organophosphate) | 0.2-5.0% | 1.0% |
| Choice of Synergist: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

Table 6 lists the main components along with a range for each components and preferred percentage for larvicidal coating.

TABLE 6

| Main Ingredients | Choice Ingredients | Preferred Range | Preferred Exemplary Amount |
|---|---|---|---|
| Coating (choice of one) | | 88.0-99.9999% | 99.82% |
| | Acrylic paint | | |
| | Oil based paint | | |
| | Plastic polymer | | |
| Choice of Larvicidal Active Ingredients: | | 0.0001-2% | 0.01% |
| | Bacillus thuringiensis israelensis | 0.0001-2% | 0.01% |
| | Methoprene | 0.0001-2% | 0.01% |
| | Pyroproxifen | 0.0001-2% | 0.01% |
| | Spinosad | 0.0001-2% | 0.01% |
| Choice of 1-3 Synergists: | | 0-10.0% | 0.7% |
| | Piperonyl Butoxide | 0-10.0% | 0.7% |
| | MGK-264 | 0-10.0% | 1.4% |
| | Etofenprox | 0-5.0% | 0.7% |
| | Pyrethrins | 0-5.0% | 0.7% |

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A dual action container for solely killing adult mosquitoes and their larvae, comprising:
   a single housing consisting of a closed bottom and closed side walls with an interior wall surface and open top;
   at least one drain opening solely along a horizontal line in the housing substantially midway between the closed bottom and open top;

an adulticidal coating layer substantially lining most of the interior wall surface of the single housing above the at least one drain opening along the midway horizontal line in the single housing; and a larvicidal coating layer substantially lining most of the interior wall surface of the single housing below the at least one drain opening along the midway horizontal line in the single housing, wherein the adulticidal coating and the larvicidal coating kill both adult mosquitoes and their larvae over time, and wherein the at least one drain opening prevents water from completely filling the single housing.

2. The dual action container of claim 1, wherein the adulticidal coating includes:
permethrin.

3. The dual action container of claim 1, wherein the larvicidal coating includes:
pyriproxyfen.

4. The dual action container of claim 1, wherein at least one of the adulticidal coating and the larvicidal coating includes a mixture for a insecticide that does not break down.

5. The dual action container of claim 1, wherein at least one of the adulticidal coating and the larvicidal coating includes an additive for allowing a slow time release of an insecticide.

6. The dual action container of claim 1, wherein the adulticidal coating contains insecticide that kills adult mosquitoes as they land to lay eggs, and the larvicidal coating that kills larval mosquitoes which emerge from the eggs.

7. The dual action container of claim 1, wherein at least one of the adulticidal coating and the larvicidal coating includes a color which attracts the insects to the coating.

8. The dual action container of claim 1, wherein at least one of the adulticidal coating and the larvicidal coating, stabilizes synergists to overcome insecticide resistance in insects.

9. The dual action container of claim 1, wherein at least one of the adulticidal coating and the larvicidal coating includes a paint.

10. The dual action container of claim 1, wherein at least one of the adulticidal coating and the larvicidal coating includes a plastic coating.

11. The dual action container of claim 1, wherein at least one of the adulticidal coating and the larvicidal coating includes a plastic impregnation.

12. The dual action container of claim 1, wherein the adulticidal coating is an insecticide selected from one of a pyrethroid, organophosphate or carbamate.

13. The dual action container of claim 12, wherein the pyrethroid is selected from one of permethrin, cypermethrin, deltamethrin or bifenthrin.

14. The dual action container of claim 12, wherein the organophosphate is selected from one of chlorpyrifos or diazinon.

15. The dual action container of claim 12, wherein the carbamate is propoxur.

16. The dual action container of claim 12, wherein the adulticidal coating includes a synergist selected from one of piperonyl butoxide, MGK-264, etofenprox, and pyrethrins.

17. The dual action container of claim 1, wherein the larvicidal coating is an insecticide selected from one of a *Bacillus thuringiensis israelensis*, methoprene, pyroproxifen or spinosad.

18. The dual action container of claim 17, wherein the larvicidal coating includes a synergist selected from one of piperonyl butoxide, MGK-264, etofenprox, and pyrethrins.

19. A dual action container for solely killing adult mosquitoes and their larvae, comprising:

a single housing consisting of a closed bottom and closed sidewalls with an interior wall surface, and open top;

at least one drain opening solely along a horizontal line in the housing substantially midway between the closed bottom and open top;

a combined coating layer that contains an adulticide and a larvicide, the combined coating layer located substantially lining most of the interior wall surface of the housing both above and below the at least one drain opening along the substantially midway horizontal line in the single housing, wherein the combined coating kills both adult mosquitoes and their larvae over time, and wherein the at least one drain opening prevents water from completely filling the single housing.

20. The dual action container of claim 19, wherein the larvicide includes:
pyriproxyfen.

21. The dual action container of claim 19, wherein the adulticide includes:
permethrin.

22. The dual action container of claim 19, wherein the combined coating includes:
permethrin and pyriproxyfen.

23. The dual action container of claim 19, wherein the combined coating includes a mixture for a long lasting insecticide that does not break down.

24. The dual action container of claim 19, wherein the combined coating includes an additive for allowing a slow timed release of an insecticide.

25. The dual action container of claim 19, wherein the combined coating includes a color which attracts the insects to the coating.

26. The dual action container of claim 19, wherein the combined coating stabilizes synergists to overcome resistance.

27. The dual action container of claim 19, wherein the combined coating includes a paint.

28. The dual action container of claim 19, wherein the combined coating includes a plastic coating.

29. The dual action container of claim 19, wherein the combined coating includes a plastic impregnation.

30. The dual action container of claim 19, wherein the adulticide in the combined coating is an insecticide selected from one of a pyrethroid, organophosphate or carbamate.

31. The dual action container of claim 30, wherein the pyrethroid is selected from one of permethrin, cypermethrin, deltamethrin or bifenthrin.

32. The dual action container of claim 30, wherein the organophosphate is selected from one of chlorpyrifos or diazinon.

33. The dual action container of claim 30, wherein the carbamate is propoxur.

34. The dual action container of claim 30, wherein the larvicide in the combined coating is an insecticide selected from one of a *Bacillus thuringiensis israelensis*, methoprene, pyroproxifen and spinosad.

35. The dual action container of claim 19, wherein the combined coating layer consists of a single lining combining the adulticide and the larvicide.

* * * * *